US006743187B2

(12) United States Patent
Solomon et al.

(10) Patent No.: US 6,743,187 B2
(45) Date of Patent: Jun. 1, 2004

(54) CONTROL DEVICE FOR THE THERAPEUTIC MOBILIZATION OF JOINTS

(75) Inventors: Alexander G. Solomon, Mississauga (CA); Jeffrey J. Culhane, Phoenix, AZ (US); Daniel E. C. Cotterell, Ajax (CA)

(73) Assignee: OrthoRehab, Inc., Lowell, MA (US)

( * ) Notice: Subject to any disclaimer, the term of this patent is extended or adjusted under 35 U.S.C. 154(b) by 0 days.

(21) Appl. No.: 09/805,465

(22) Filed: Mar. 14, 2001

(65) Prior Publication Data

US 2001/0047209 A1 Nov. 29, 2001

Related U.S. Application Data

(60) Provisional application No. 60/189,030, filed on Mar. 14, 2000.

(51) Int. Cl.[7] .................................... A61B 5/103
(52) U.S. Cl. .................................... 600/587; 600/595
(58) Field of Search .................................... 600/587, 595; 601/26; 482/4–9; 73/862.044, 862.045, 760, 172, 379.01

(56) References Cited

U.S. PATENT DOCUMENTS

| | | | | |
|---|---|---|---|---|
| 2,666,262 A | | 1/1954 | Ruge | |
| 4,616,511 A | * | 10/1986 | Gindy et al. | 177/211 |
| 4,637,263 A | * | 1/1987 | Fritz et al. | 73/862.044 |
| 4,691,694 A | | 9/1987 | Boyd et al. | |
| 4,889,108 A | * | 12/1989 | Bond et al. | 482/9 |
| 5,186,695 A | | 2/1993 | Mangseth et al. | |
| 5,230,252 A | | 7/1993 | O'Brien et al. | |
| 5,244,441 A | * | 9/1993 | Dempster et al. | 482/9 |
| 5,255,188 A | | 10/1993 | Telepko | |
| 5,437,587 A | | 8/1995 | Prince et al. | |
| 5,951,499 A | * | 9/1999 | Saringer et al. | 601/33 |
| 6,162,189 A | * | 12/2000 | Girone et al. | 482/79 |

FOREIGN PATENT DOCUMENTS

| | | |
|---|---|---|
| CH | 353555 | 5/1961 |
| DE | 1206622 | 12/1965 |
| FR | 2619723 | 3/1989 |
| WO | 9718787 | 5/1997 |

* cited by examiner

*Primary Examiner*—Charles Marmor
(74) *Attorney, Agent, or Firm*—Nancy E. Hill; Hill & Schumacher

(57) ABSTRACT

A control system is adapted for use In association with a therapeutic motion and splinting device. The therapeutic device has at least one component that is monitored. The system comprises the steps of defining the range of motion, defining the maximum reverse on load, monitoring the reverse on load and moving the device through its range of motion. A first and second maximum limit of range of motion in a first and second direction are respectively defined. A maximum reverse on load is defined and is monitored whereby the deformation of the at least one component is monitored and the load created is interpreted. The device is cycled between a first and second position defined by one of the first maximum limit and the maximum reverse on load and one of the second maximum limit and the maximum reverse on load respectively.

9 Claims, 7 Drawing Sheets

CONTROL DEVICE FOR THE THERAPEUTIC MOBILIZATION OF JOINTS

CROSS REFERENCE TO RELATED PATENT APPLICATION

This patent application relates to U.S. Provisional Patent Application Serial No. 60/189,030 filed on Mar. 14, 2000 entitled CONTROL DEVICE FOR THE THERAPEUTIC MOBILIZATION OF JOINTS.

FIELD OF THE INVENTION

This invention relates to a control device for use in association with the therapeutic mobilization and positioning devices of joints and in particular a control device that measures the force through the interpretation of the deformation in at least one component in the therapeutic mobilization device where the force is the force acting on the patient by the device or the force of the patient acting on the device or a combination of the forces.

BACKGROUND OF THE INVENTION

The use of therapeutic mobilization devices is well known in the rehabilitation and treatment of injured joints and the surrounding soft tissue. Therapeutic mobilization devices have been used In association with continuous passive motion (CPM) control systems such that the joint is moved continuously over a predetermined path for a predetermined amount of time. An alternative protocol includes dynamic serial splinting or static serial splinting.

CPM and splinting entails moving the joint via its related limbs through a passive controlled range of motion without requiring any muscle coordination. Active motion is also beneficial to the injured joint, however muscle fatigue limits the length of time the patient can maintain motion or a position, therefore a device that provides continuous passive motion to the joint or progressive splinting is essential to maximize rehabilitation results. Numerous studies have proven the clinical efficacy of CPM to accelerate healing and maintain range of motion. Static Progressive Splinting (SPS) and Dynamic Splinting (DS) are accepted and effective treatment modalities for the management and modelling of soft tissue surrounding articulations. Both SPS and DS have been proven efficacious and are supported by clinical studies. CPM, SPS and DS are integral components of a successful therapy protocol.

However, none of the prior art devices show a device that automates a progressive stretch and relaxation protocol. That is none of the control systems can be adapted to progressive splinting of a patient so as to manipulate their limb to its end range of motion and hold in that position. After the patient relaxes and the soft tissue has stretched the patient can continue in the same direction of travel to achieve greater range of motion (ROM). Previously this was done with static or dynamic splints.

SUMMARY OF THE INVENTION

A control system is adapted for use in association with a therapeutic motion and splinting device. The therapeutic device has at least one component that is monitored. The system comprises the steps of defining a first maximum limit of range of motion in a first direction for the device; defining a second maximum limit of range of motion in a second direction for the device; defining a maximum reverse on load for the device; monitoring a reverse on load on the at least one component of the device including monitoring the deformation of the at least one component and interpreting the load created between the patient and the at least one component; first moving the device in the first direction of travel to a first position defined by one of the first maximum limit and the maximum reverse on load; second moving the device in the second direction of travel to a second position defined by one of the second maximum limit and the maximum reverse on load; and repeating the first and second moving steps.

In another aspect of the invention there is provided a strain gauge chassis for use in a control system for a therapeutic motion device. The strain gauge comprises a chassis and at least a first pair of strain gauges. The chassis is adapted to be attached to at least one component of the therapeutic motion device. The chassis has a base, a top portion, and first and second spaced apart side walls extending therebetween. The first pair of strain gauges are attached to opposing sides of the first side wall of the chassis and define a first bridge whereby the reverse on load of the at least one component of the therapeutic motion device is determined by monitoring the strain gauges and determining the deformation of the component and interpreting the load created between the patient and the component.

In a further aspect of the invention there is provided a strain gauge chassis for use in a control system for a therapeutic motion device. The strain gauge comprises at least one pair of strain gauges adapted to be attached to at least one component of the therapeutic motion device. The pair of strain gauges define a first bridge whereby the reverse on load of the at least one component is determined by monitoring the strain gauges and determining the deformation of the component and interpreting the loads created between the patient and the component.

In a typical CPM mode the range of motion (ROM) is defined and the device operates through a pre-defined range. In contrast in progressive stretch relaxation (PSR) a defined reverse on load force is applied to the limb and the device seeks the maximum range of motion. Sensitive reverse on load force monitoring throughout the range of motion is critical in providing safe and efficacious motion. PSR will progressively find the maximum range of motion in each cycle in sequential steps. PSR will rely on the patient's natural relaxation response and the plastic properties of soft tissue surrounding the joint. In progressive splinting a patient has their limb manipulated to its end range of motion and held in that position. After the patient relaxes and the soft tissue has stretched the patient can continue in the same direction of travel to achieve greater ROM. The sensitive strain gauges in the device will be able to monitor the reverse on load (ROL) force and relaxation response of the patient and soft tissue and continue in the direction of travel. PSR will sequentially increase the load applied to the limb up to a defined maximum safe load. The device will drive the limb through its range of motion to the first sequential targeted ROL and monitor the force until it relaxes to a predefined value of the first sequential target. If the target relaxed load value is attained before the defined pause time the device increases its target sequential ROL and continues to drive the limb in the direction of travel. Once again the device monitors the ROL at the limb and waits for a relaxation response to increase the sequential target load. Once the maximum sequential target load is achieved the device repeats the cycle in the opposite direction of travel. If the target sequential load is not achieved within the pause time the device changes direction of travel and continues with the first targeted sequential load. If the patient resists motion or applies a load onto the device greater than the maximum preset ROL the device reverses direction.

The control system will allow the therapeutic device to be operated in CPM or PSR mode. In PSR mode the device's primary operating parameter is the reverse on load (ROL). In PSR mode the maximum safe ROM is programmed to limit the absolute ROM a joint will experience. Whereby a safe and effective load is applied to the joint allowing the joint to experience its maximum range of motion each cycle. The objective of PSR is to accelerate achieving the ROM goals for the particular joint. PSR represents the microprocessor controlled electromechanical embodiment of progressive splinting. Progressing splinting is a common and efficacious therapy modality often used in conjunction with CPM.

Further features of the invention will be described or will become apparent in the course of the following detailed description.

BRIEF DESCRIPTION OF THE DRAWINGS

The invention will now be described by way of example only, with reference to the accompanying drawings, in which.

DETAILED DESCRIPTION OF THE INVENTION

Figure 1:
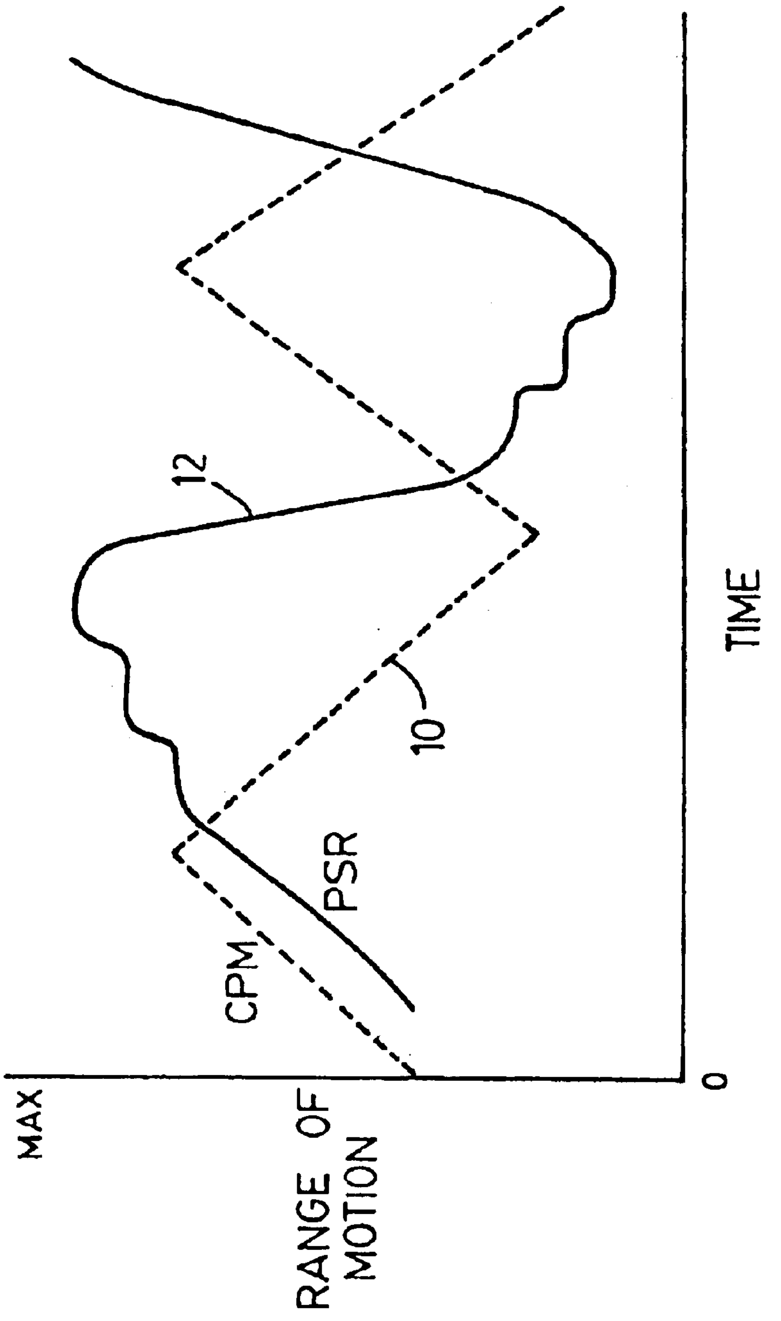
FIG. 1 is a graphical representation of the range of motion against time for a CPM device as compared to a PSR device each using a control device constructed in accordance with the present invention.
Figure 2:
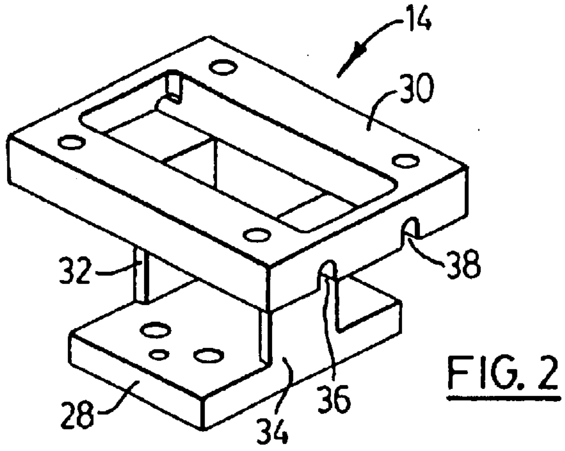
FIG. 2 is a perspective view of load cell chassis for use in association with the control system of the present invention.
Figure 3:
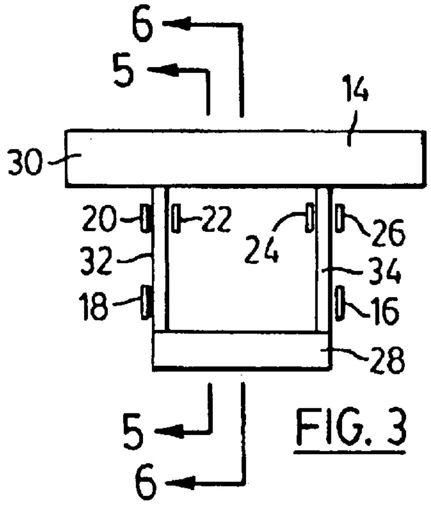
FIG. 3 is a side view of the load cell chassis of FIG. 2.
Figure 4:
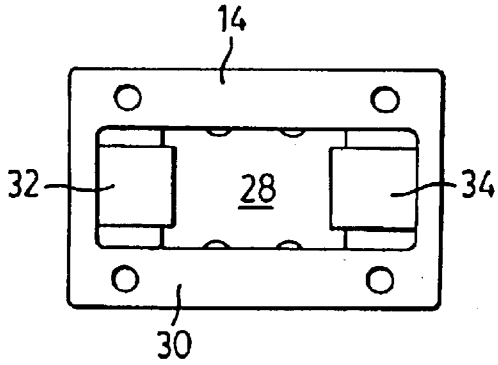
FIG. 4 is a top view of the load cell chassis of FIG. 2.
Figure 5:
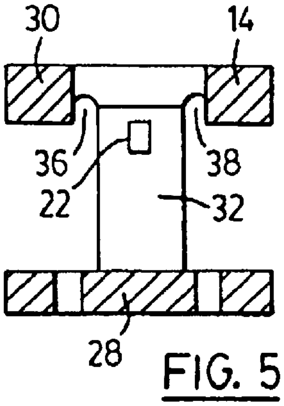
FIG. 5 is a section view of the load cell chassis taken along line 5—5 in FIG. 3.
Figure 6:
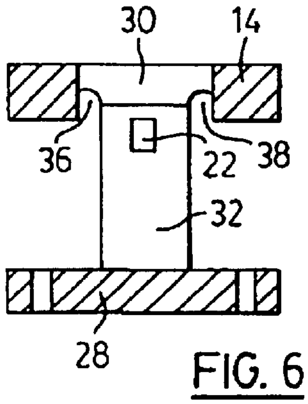
FIG. 6 is a section view of the load cell chassis taken along line 6—6 in FIG. 3.

FIG. 1 shows a typical graph of the range of motion against time for a progressive splint relaxation (PSR) mode 12 as compared to a continuous passive motion mode (CPM) 10. As can be seen in the graph with the CPM mode the range of motion (ROM) Is defined and the device operates through a defined constant range. In contrast in a progressive stretch relaxation mode (PSR) a defined load is applied to the limb and the device seeks the maximum range of motion for each cycle. In PSR mode the patient has their limb manipulated to its end range of motion and held in that position. After the patient relaxes and the soft tissue has stretched the patient can continue in the same direction of travel to achieve greater ROM.

Referring to FIGS. 2 to 6 a load cell chassis is shown generally at 14. The load call chassis and the load cells attached thereto are configured to interpret the torque and force applied to a patient's limb. Six load cells or strain gauges 16, 18, 20, 22, 24 and 26 are attached to chassis 14 The load cells are configured to form three electrical bridges. Specifically the first bridge is formed by load cells 16 and 18, the second bridge by load cells 20 and 22 and the third bridge by load cells 24 and 26.

Chassis 14 includes a base 28, a top portion 30, and sides 32 and 34. Notches 36 and 38 are positioned to amplify the force and torque distributed along sides 32 and 34 to achieve predictable outputs from the strain gauges 16, 18, 20, 22, 24 and 26.

Figure 7:
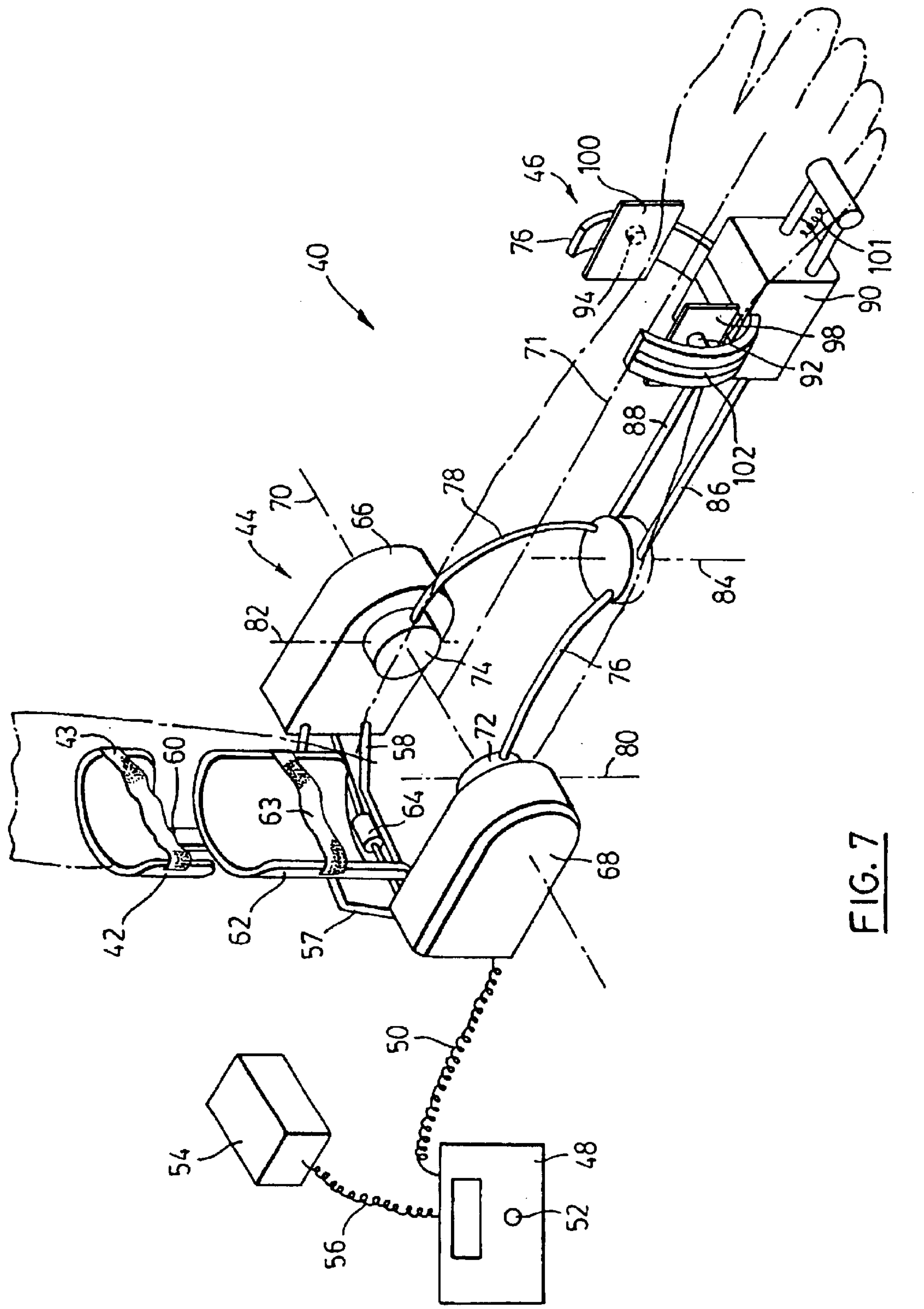
FIG. 7 is a perspective view of a combination pro/supination and flexion therapeutic mobilization device including the control system of the present invention.

An example of a therapeutic motion device using the chassis described above is shown in FIG. 7 generally at 40. The therapeutic motion device 40 includes an upper arm or proximal humerus support 42, an elbow or flexion actuator assembly 44 and a wrist or pro/supination actuator assembly 46. The therapeutic motion device 40 shown herein forms a separate invention which is co-pending, accordingly it will only be briefly described herein and only as it relates to the control device of the present invention.

Therapeutic motion device 40 is electrically connected to a patient controller 48 by cord set 50. Switch 52 on patient controller 48 turns device 40 off and on. Patient controller 48 is connected to a power supply 54 via cable 56. Patient controller 48 contains rechargeable batteries and can supply power to device 40 with or without being connected to a wall outlet.

Proximal humerus support 42 and distal humerus support 62 is rigidly fixed to the orthosis via parallel rods 57 and 58. Adjustable support 60 is telescopically connected to parallel rod 57 and 58 and supports proximal humeral cuff 42.

Flexion actuator assembly 44 includes actuators 66 and 68 the relative position of which are adjusted by barrel nut 64 which is threadedly attached thereto. When rotated barrel 64 forces actuators 66 and 68 to move relative to each other in a parallel fashion while still sharing axis 70. Actuators 66 and 68 are slidably mounted onto parallel rods 57 and 58. Parallel rods 57 and 58 each have a portion that is angled such that when the distance increases between actuators 66 and 68 so does the distance between axis 70 and humeral cuffs 42 and 62. This accommodates variations in arm sizes for alignment purposes. Drive elbow flexion actuator 68 and idler elbow actuator 66 have respective output rotating shafts 72 and 74. The output shafts 72 and 74 rotate in a concentric fashion with the orthosis anatomic elbow axis 70. Drive stays 76 and 78 are pivotally connected to output shafts 72 and 74 and pivot through the axis shown at 80 and 82. The drive stays 76 and 78 are connected at their distal ends and share a common pivot 84. Pivot 84 compensates for the variations in patient's Valgus carrying angle and the adjustable distance between the elbow actuators. Two parallel rods 86 and 88 are suitably fixed to the pivot 84.

The pro/supination assembly includes a housing 90 which is slidably mounted to rods 86 and 88. Screw mechanisms 92 and 94 are mounted to the inside of ring 96. Softgoods 98 and 100 are pivotally mounted to screw mechanisms 92 and 94 and can be adjusted to compensate for variations in the size of a patient's distal radius and ulna as well as centering the patient's limb along the pro/supination axis 71. Ring 96 has a center and its center is concentric with pro/supination axis 71. Ring 96 is slidably mounted in housing 90. External drive belt 102 moves the ring 96 in a rotational fashion relative to housing 90.

Figure 8:
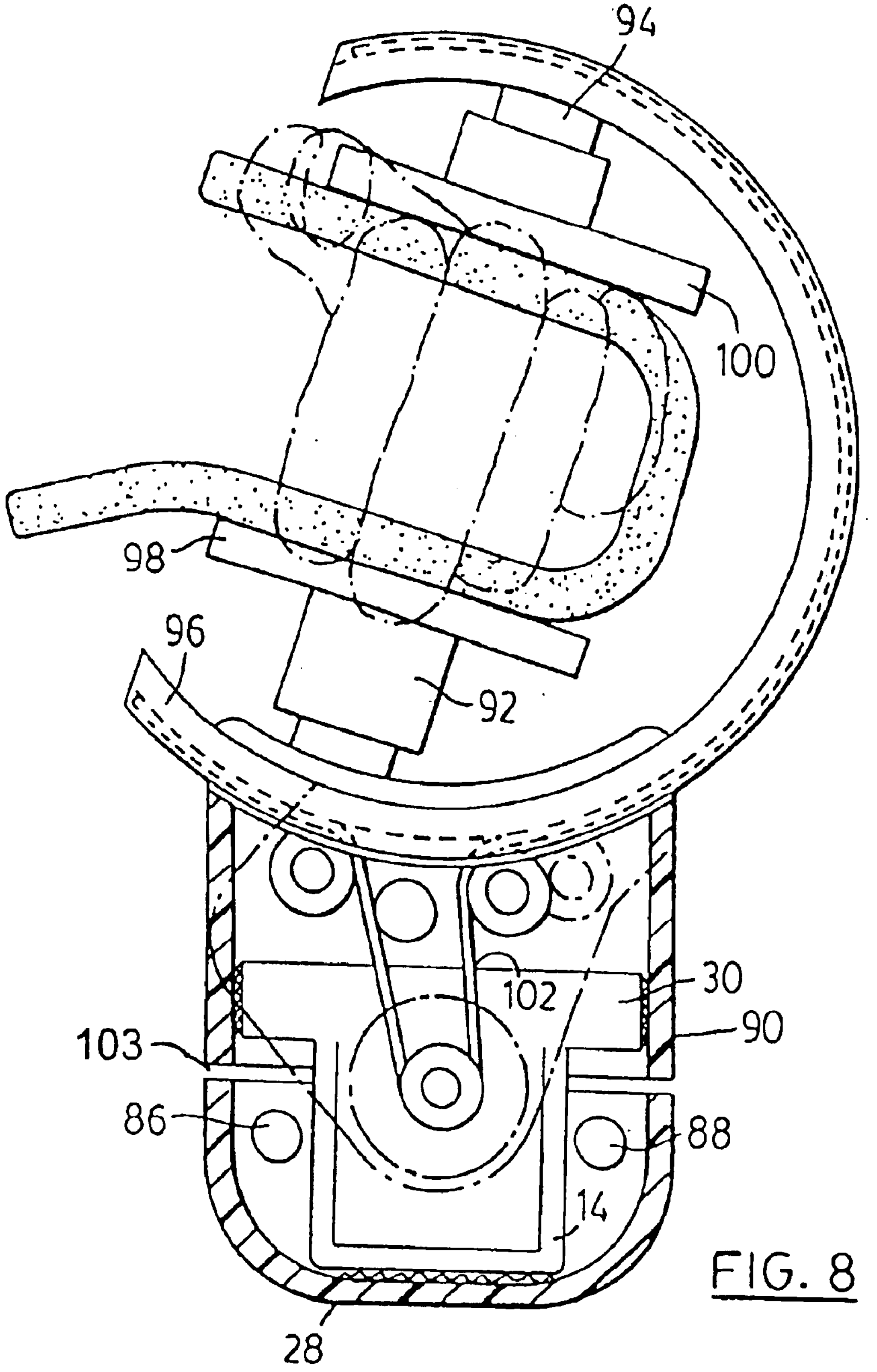
FIG. 8 is a front view of the pro/supination assembly of the therapeutic mobilization device of FIG. 7 shown with the load cell chassis of the control system of the present invention.

Base 28 of chassis 14 is suitably fixed to housing 90 as shown in FIG. 8. The ring 96 is mechanically connected to the top 30 of the chassis 14 and mechanically isolated. Housing 90 has a break therein shown in FIG. 8 at 103 such that the base of housing 90 is mechanically isolated from the top of housing 90 through chassis 14. The sides of the load cell chassis are configured in a fashion to predictably respond to loads in the direction and scale proportionate to the loads experienced during rehabilitation.

In the PSR mode the device will sequentially increase the ROL applied to the limb up to a defined maximum safe load. The device will drive the limb through its range of motion to the first sequential targeted ROL and monitor the load until it relaxes to a predefined value of the first sequential target. If the target relaxed load value is attained before the defined pause time, the device increases its target sequential ROL and continues to drive the limb in the direction of travel. Once again the device monitors the loads at the limb and waits for a relaxation response to increase the sequential target load. Once the maximum sequential target load is achieved the device repeats the cycle in the opposite direction of travel. If the target sequential ROL is not achieved within the pause time the device changes direction of travel and continues with the first targeted sequential load.

Force is interpreted in a simple fashion by the second bridge (load cells 22 and 24) and the third bridge (load cells 26 and 20). Torque is interpreted by monitoring the difference between the second and third bridges. The first bridge (load cells 16 and 18) is monitored to compensate for variations in the device's position as gravity acts differently when the position of the device and limb changes throughout the range of motion.

A method of creating distraction at the elbow joint throughout the range of motion of the elbow may be integrated Into the existing device's orthosis. A single adjustable tension member 101 may be secured between the housing of the pro/supination drive in housing 90 and the end of the parallel rods 86, 88. The tension member 101 may deliver continuous distraction where there is no change in the amount of torque as the elbow travels through its range of motion. With the proximal portion connected to the pro/supination housing 90 and the distal portion of tension member 101 connected to the end of the device, when the devices pro/supination fixation method is secure the elbow will undergo distraction. The elbow is held relative to axis 70 and humeral cuffs 42 and 62 by straps 63 and 43.

Similar results can be achieved by placing compressive members on the proximal side of the pro/supination housing 90 where by the proximal portion of the compressive member is secured along the parallel rods 86, 88 and the distal portion of said compressive member is pushing against the proximal portion of the pro/supination housing 90.

In use the device described above may be used in a PSR mode wherein the device will progressively find the maximum range of motion in each cycle in sequential steps. PSR will rely on the patient's natural relaxation response and the plastic properties of soft tissue surrounding the joint. In progressive splinting a patient has their limb manipulated to its end range of motion and held in that position. After the patient relaxes and the soft tissue has stretched the patient can continue in the same direction of travel to achieve greater ROM. The strain gauge cells in the device will be able to monitor the relaxation response of the patient and soft tissue and continue in the direction of travel. PSR will sequentially increase the load applied to the limb up to a defined maximum safe load. The device will drive the limb through its range of motion to the first sequential targeted ROL and monitor the ROL until it relaxes to a predefined value of the first sequential target. If the target relaxed load value is attained before the defined pause time the device increases its target sequential ROL and continues to drive the limb in the direction of travel. Once again the device monitors the loads at the limb and waits for a relaxation response to increase the sequential target load. Once the maximum sequential target load is achieved the device repeats the cycle in the opposite direction of travel. If the target sequential load is not achieved within the pause time the device changes direction of travel and continues with the first targeted sequential ROL. The above description discloses the control system wherein force and torque are monitored. It will be appreciated by those skilled in the art that the system is not limited to only monitoring force or torque. Accordingly the above described control system may be adapted so as to control and interpret forces created by a therapeutic motion device and administered to a patient whereby the control system monitors the deformation of a component fixed to such a device.

The interpretation and control of force can be monitored in a single or multiple plane configurations, in a rotational motion or in a combined rotational and planer motion. The control and interpretation can be the result of discrete deformation of a component to interpret a force or forces or combined deformation of several components. The control and interpretation of a force or forces can also be the result of monitoring the deformation of component in multiple locations.

A uniplaner motion is representative of the motion of the knee, wrist, ankle, spine, digits, hip, shoulder and elbow. All of these joints are capable of uniplaner motion. The method of interpreting and controlling the forces related to uniplaner motion are completed in the simplest fashion by securing and supporting the anatomical feature or limb on the distal and proximal portions of a joint. Whereby one of the support structures for the distal or proximal portions is mechanically isolated. The deformation of a component to interpret and control the force administered to the joint is mechanically isolated and independently connects the proximal or distal support structure to the device administering the force to the limb. It will be appreciated by those skilled in the art that the forces with respect to the patient/device interface can occur without mechanical isolation, however this will result in a grosser monitoring of the interacting forces.

Figure 9:
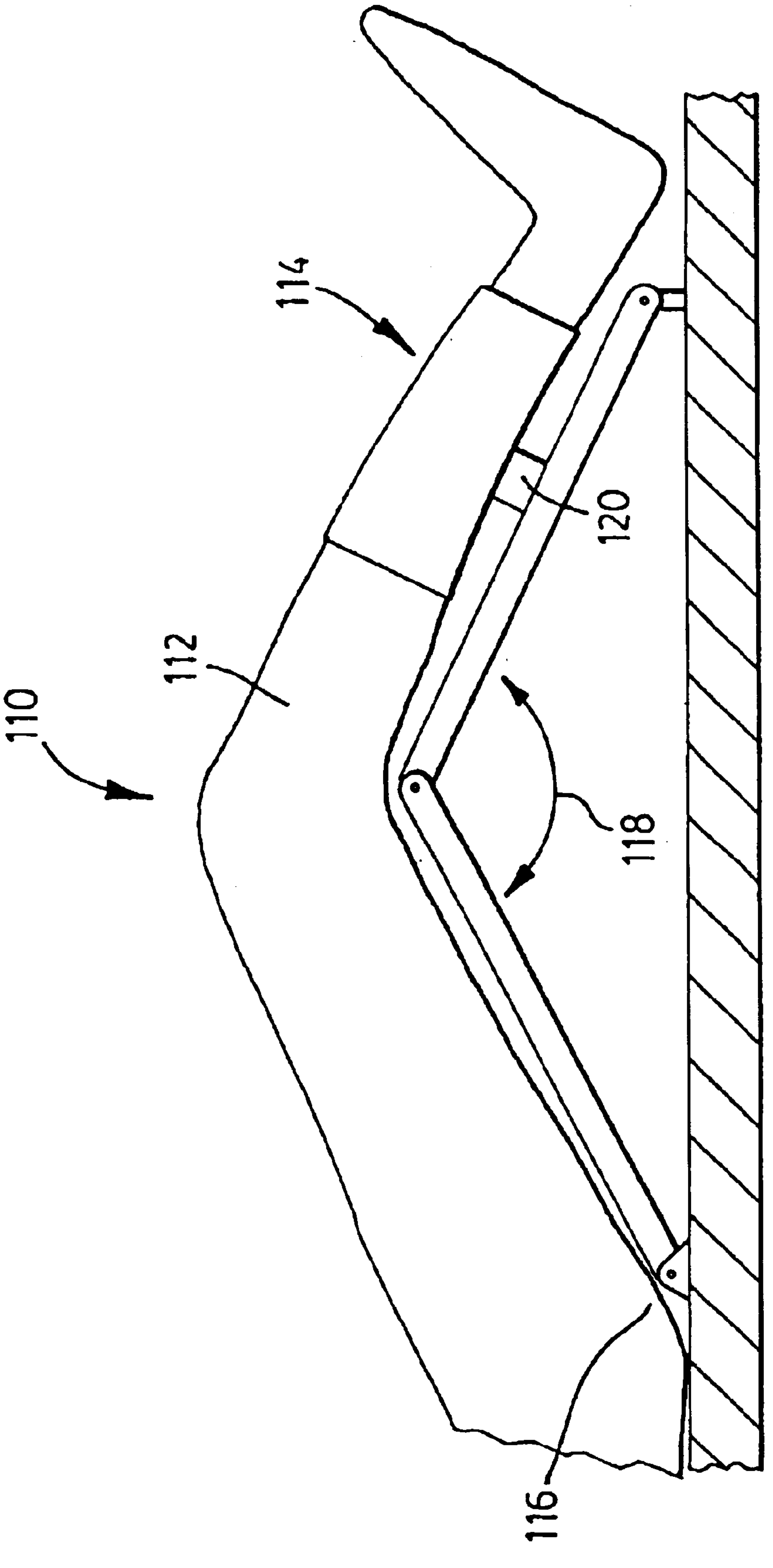
FIG. 9 is a side view of a knee therapeutic motion device using the control system of the present invention.

Referring to FIG. 9 an example of a uniplanar motion device is shown generally at 110. Device 110 is adapted for use on a leg 112 and the device includes a distal support 114 and a proximal support 116. The relative motion of these supports is shown at 118. The mechanically isolated component is shown at 120.

Torque or rotational motion is representative of but not limited to the shoulder, forearm and hip. It should be noted that most uniplaner motion occurs about a single axis and may be considered torque although it is usually considered planer vs. rotational motion. In applications of torque the same principles apply as in uniplaner motion. The component identified to monitor the deformation or to interpret and control torque should be mechanically isolated and be responsible for delivering the torque between the proximal and distal portions of the device. A single or multiple components may be used to interpret and control the torque or a plurality of components may be monitored in multiple locations.

Figure 10:
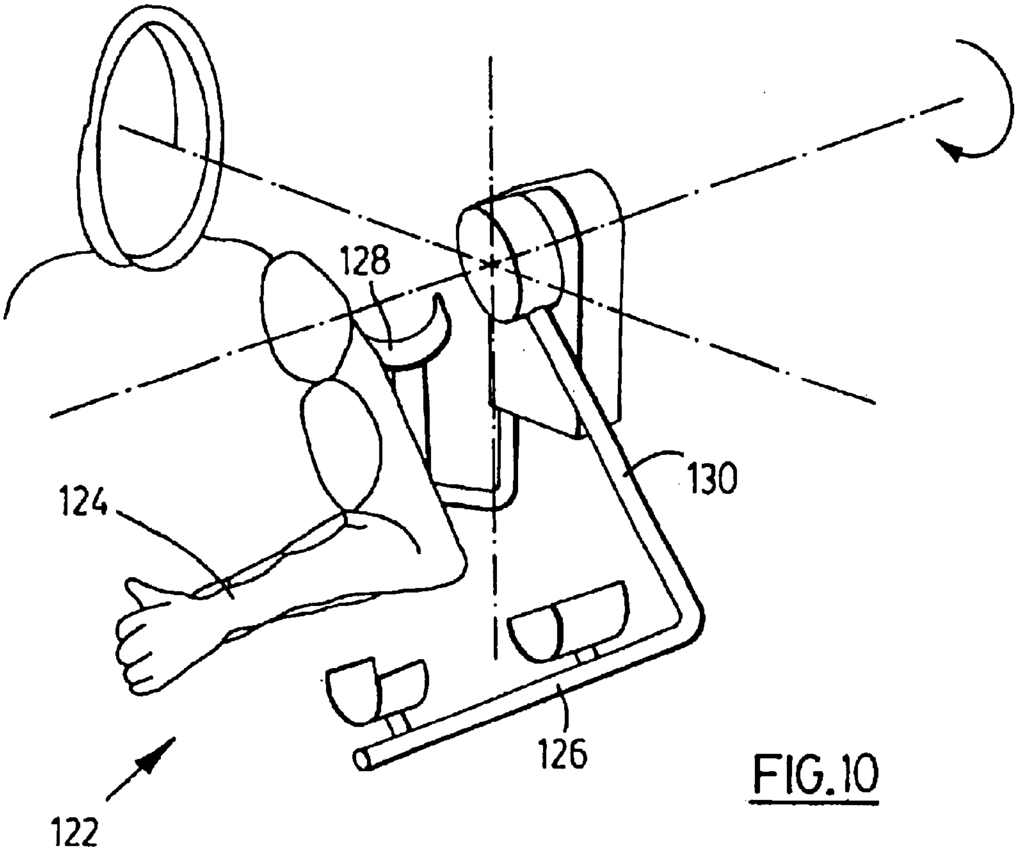
FIG. 10 is a perspective sketch of a shoulder therapeutic motion device using the control system of the present invention.

Referring to FIG. 10 an example of a rotational motion device is shown generally at 122. Device 122 is adapted for use on an arm 124 and the device includes a distal support 126 and a proximal support 128. An example of the mechanically isolated component is shown at 130.

Figure 11:
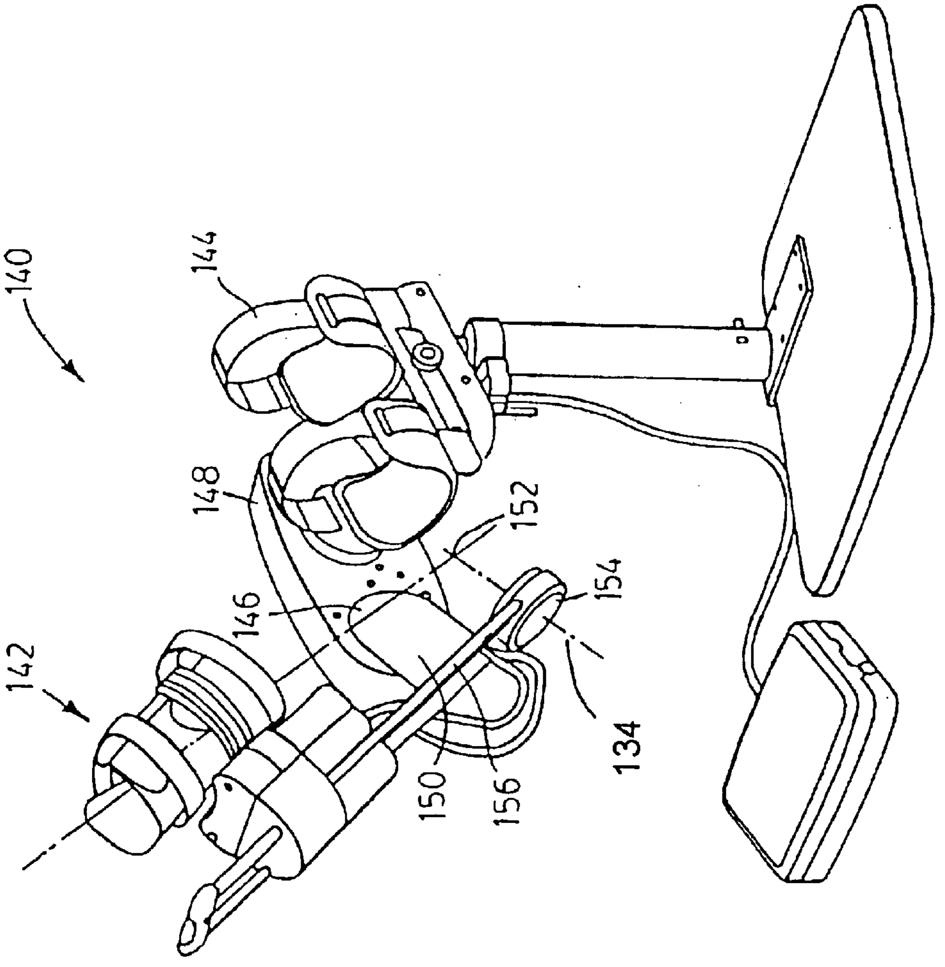
FIG. 11 is a perspective view of an alternate embodiment of a combination pro/supination and flexion therapeutic mobilization device including the control system of the present invention.

Referring to FIG. 11, an alternate embodiment of a combination pro/supination and flexion mobilization device is shown at 140. The device is similar to that shown in FIGS. 7 and 8. Device 140 includes a pro/supination assembly 142 similar to that described above in regard to device 40. However, the flexion actuator assembly 144 is somewhat different than that described above with regard to device 40. The flexion actuator assembly 144 includes an orthosis stay 146 and is pivotally connected to actuator 148 at 150 and pivots around the elbow flexion rotational axis 152. Pivot point 150 of orthosis stay 146 is concentric with the elbow pivot axis 134. Orthosis stay 146 is pivotally connected at one end to actuator 140. The distal end of orthosis stay 146 is connected to valgus pivot 154. Pro/supination assembly 142 is attached to valgus pivot 154 via rods 156. As with device 40 load cells are positioned in pro/supination assembly 142.

With all of the therapeutic motion devices it is important to align the device appropriately such that the patient's joints are aligned with the pivot points on the therapeutic devices.

It will be appreciated that the above description relates to the invention by way of example only. Many variations on the invention will be obvious to those skilled in the art and such obvious variations are within the scope of the invention as described herein whether or not expressly described.

What is claimed as the invention is:

1. A method of controlling a therapeutic motion and splinting device, the device having at least one movable portion that moves relative to a fixed portion and one of the at least one movable portion and the fixed portion having at least one component that is capable of deformation and the device being adapted for use with a patient whereby movement of the at least one moveable portion creates a load between the patient and the at least one component, comprising the steps of:

defining a first maximum limit of range of motion in a first direction for the device;

defining a second maximum limit of range of motion in a second direction for the device;

defining a maximum reverse on load for the device;

monitoring a reverse on load on the at least one component of the device including monitoring the deformation of the at least one component and interpreting the load created between the patient and the at least one component;

first moving the at least one movable portion of the device in the first direction of travel to a first position defined by one of the first maximum limit and the lesser of a predetermined sequential target reverse on load and a predetermined maximum safe load;

second moving the at least one movable portion of the device in the second direction of travel to a second position defined by the second maximum limit and the lesser of a predetermined sequential target reverse on load and a predetermined maximum safe load; and repeating the first and second moving steps:

wherein the first moving step includes pausing at the first position for a predetermined length of time and monitoring the load, wherein the load decreases due to a relaxation response of the patient, determining if the relaxed load is less than a predetermined relaxation load and if less than the predetermined relaxation load then moving the at least one movable portion of the device to an extended first position defined by one of the first maximum limit and the lesser of an extended reverse on load and the maximum safe load and if the load between the patient and the at least one component is not less than the predetermined relaxation load then proceeding to the next step and wherein the second moving step further includes pausing at the second position for a predetermined length of time and monitoring the load, wherein the load decreases due to a relaxation response of the patient, determining if the load between the patient and the at least one component is less than a predetermined relaxation load and if less than the predetermined relaxation load then moving the at least one movable portion of the device to an extended second position defined by one of the second maximum limit and the lesser of an extended reverse on load and the maximum safe load and if the load between the patient and the at least one component is not less than the predetermined relaxation load then proceeding to the next step.

2. A method as claimed in claim 1 wherein the first moving step and second moving step include sequentially moving the at least one movable portion of the device and pausing a predetermined number of times.

3. A method as claimed in claim 2 wherein the load is monitored using a strain gauge chassis having a base, a top portion, and first and second spaced apart side walls extending therebetween; a first pair of strain gauges attached to the opposing sides of the first side wall and defining a first bridge; and a second pair of strain gauges attached to opposing sides of the second side wall and defining a second bridge and wherein the load created between the patient and the at least one component is monitored by interpreting the first and second bridges to determine a force and interpreting the difference between the first and second bridges to determine a torque.

4. A method as claimed in claim 3 wherein the chassis further includes a third pair of strain gauges including one attached to one side of the first side wall and one attached to the opposing side of the second side wall and defining a third bridge wherein the load is monitored by further interpreting the third bridge and adjusting the load to compensate for the position of the at least one component.

5. A method as claimed in claim 1 further including the step of monitoring the deformation of a plurality of components of the device.

6. A method as claimed in claim 1 wherein the load that is monitored is torque.

7. A method as claimed in claim 1 wherein the load that is monitored is force.

8. A method as claimed in claim 1 wherein the load that is monitored is both force and torque.

9. A method as claimed in claim 1 further including the step of adjusting the monitored load to compensate for variance in position of the at least one moveable portion.

* * * * *